United States Patent [19]

Frey

[11] Patent Number: 4,523,587

[45] Date of Patent: Jun. 18, 1985

[54] RETENTION DEVICE FOR CENTERING AN ENDOPROSTHESIS SHANK IN A BONE

[75] Inventor: Otto Frey, Winterthur, Switzerland

[73] Assignee: Sulzer Brothers Limited, Winterthur, Switzerland

[21] Appl. No.: 460,366

[22] Filed: Jan. 24, 1983

[30] Foreign Application Priority Data

Feb. 23, 1982 [CH] Switzerland ............... 1093/82

[51] Int. Cl.³ ............................................. A61F 5/04
[52] U.S. Cl. ..................... 128/92 C; 3/1.911; 3/1.912; 433/173
[58] Field of Search ........... 128/92 C, 92 CA, 92 BA; 3/1.9, 1.91, 1.911, 1.912, 1.913; 433/173–175, 177

[56] References Cited

U.S. PATENT DOCUMENTS

| 3,732,621 | 5/1973 | Bostrom ............................ 433/174 |
| 4,011,602 | 3/1977 | Rybicki et al. ...................... 3/1.9 |
| 4,167,047 | 9/1979 | Grundei et al. ..................... 3/1.91 |
| 4,293,962 | 10/1981 | Fuson .............................. 128/92 C |

FOREIGN PATENT DOCUMENTS

| 1961531 | 7/1970 | Fed. Rep. of Germany ........... 3/1.9 |
| 2114323 | 10/1971 | Fed. Rep. of Germany ........... 3/1.9 |
| 617412 | 2/1927 | France ............................. 433/173 |
| 560040 | 3/1975 | Switzerland ....................... 3/1.912 |

Primary Examiner—Stephen C. Pellegrino
Assistant Examiner—Gene B. Kartchner
Attorney, Agent, or Firm—Kenyon & Kenyon

[57] ABSTRACT

The retention device is formed of a guide piece for slidably receiving the shank of an endoprosthesis and an anchoring element for anchoring the guide piece within a bone. The guide piece and anchoring element can be pushed together or threaded together. The anchoring element is provided with slits so as to facilitate expansion upon movement of the guide piece into the anchoring element.

16 Claims, 3 Drawing Figures

U.S. Patent          Jun. 18, 1985          4,523,587
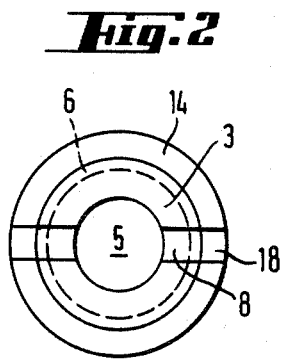
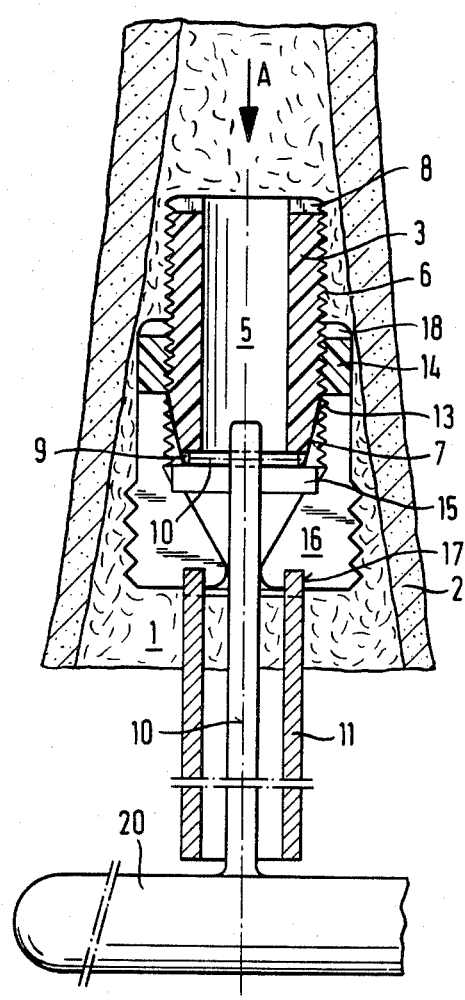
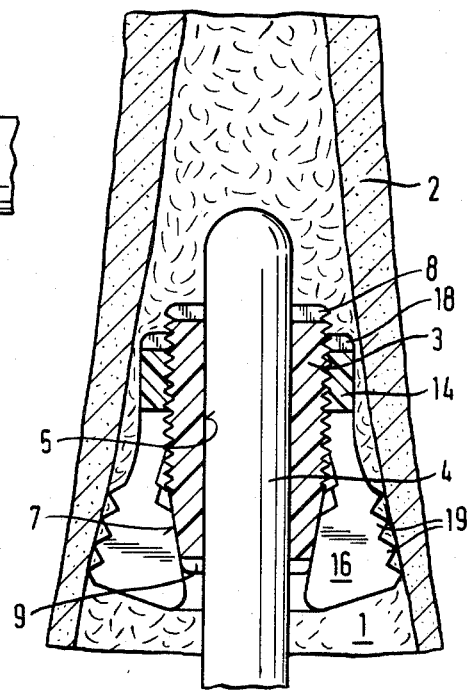

RETENTION DEVICE FOR CENTERING AN ENDOPROSTHESIS SHANK IN A BONE

This invention relates to a retention device. More particularly, this invention relates to a retention device for centering an endoprosthesis shank in a bone.

As is known, the anchoring shanks of endoprostheses, for example of knee joint prostheses, should, in many cases, be placed in a bone in such a manner as to be displaceable in an axial direction but centered in a radial direction. However, placement of the anchoring shanks in this manner may be complicated by the fact that the support of the shank which generally takes place on the cortical tissue of the bone must occur in a medullary cavity which narrows significantly in the axial direction or in a cavity which widens from the outer end. Thus, it becomes difficult to fix the anchoring shank in the bone in a centered manner.

Accordingly, it is an object of the invention to provide a retention device for radially centering a shank of a prosthesis while permitting the shank to move axially.

It is another object of the invention to provide a retention device which can be fixed in any desired region within a bone cavity.

It is another object of the invention to be able to implant an anchoring shank of an endoprosthesis in a centered and secured manner within a bone.

It is another object of the invention to provide a retention device for anchoring an endoprosthesis shank in a bone having a cavity which is of variable shape.

Briefly, the invention provides a retention device for centering an endoprosthesis shank in a bone which is comprised of a guide piece having a cavity for slidably receiving the shank in slide fit relation and an expandable anchoring element receiving the guide piece in wedge-like relationship.

The guide piece has a cross-section which is constant at least in the region where the shank is guided while the cavity is adapted to the shank at least partially in the circumferential direction.

Either or both of the guide piece and anchoring element has a surface which is tapered at least over a part of the axial length of the element, e.g. an outer shell of the guide piece or the inner periphery of the anchoring element, in order to permit expansion of the anchoring element upon movement of the guide piece into the anchoring element.

The invariance of the shank cross-section, which may, for example, be circular, elliptical or oval, and the mutual adaptation of the guide piece and shank in a slide fit insure a radial centering of the shank while permitting a simultaneous axial movement of the shank. By forming the retention device of a guide piece in a separate anchoring element, the retention device may be fixed in any desired axial region of a medullary cavity of a tubular bone into which the shank of an endoprosthesis is to be placed.

The fixation of the retention device and/or the anchoring of the shank may be accomplished without the need for a bone cement or in a cement bed which serves only as a filling for the medullary cavity. In the simpliest case, the guide piece is drawn in or hammered into the internal cavity of the anchoring element. Barb-type serrations may also be provided on the outer shell of the guide piece and/or in the inner circumference of the anchoring element in order to improve the mutual engagement of the two components against unintended release.

In order to facilitate expansion, the anchoring element is provided with a plurality of longitudinally disposed slits which extend substantially axially and/or is formed as a deformable hollow cylinder having an undular circumferential surface. Further, the tapered surfaces on the guide piece and/or anchoring element which cause expansion may have the same or different angles of taper.

If the precision with which the retention device is to be fixed in a certain axial region of a bone is high, the guide piece may be threaded into the anchoring element. In this case, there is less danger that the anchoring element will be displaced due to an axial pull or pressure.

The guide piece and anchoring element of the retention device may be made of any material which is customarily used in implant technology. For example, each component may be made of polyethylene of the classification HDPE and UHMW. Further, it is possible to provide the surfaces of the two components, at least partially, with a coating which, for example, reduces the friction of the shank in a slide fit or which promotes the accretion of tissue.

These and other objects and advantages of the invention will become more apparent from the following detailed description taken in conjunction with the accompanying drawing wherein:

FIG. 1 illustrates a cross-sectional view of a retention device according to the invention during implantation in a tubular bone;

FIG. 2 illustrates an end view of the retention device taken in the direction A of FIG. 1;

FIG. 3 illustrates the retention device of FIG. 1 with a shank of an endoprosthesis centered within a bone.

Referring to FIG. 3, the retention device is sized so as to fit into a medullary cavity 1 of a bone 2, for example, a cavity which narrows significantly in one direction, i.e. the upward direction as viewed in FIG. 3. The retention device includes a guide piece 3 and an expandable anchoring element 14 which receives the guide piece 3 in wedge-like relationship.

Referring to FIG. 1, the guide piece 3 has a central bore defining a cavity 5 for slidably receiving the shank 4 (see FIG. 3) of an endoprosthesis. To this end, the cavity 5 is adapted in form and dimensions to the cross-section of the shank 4 so that the shank 4 can be guided axially in a slide fit relationship. In the present example, the cavity 5 is of circular cross-sectional shape.

The guide piece 3 is of cylindrical shape with a thread 6 on an outer surface or shell and a tapered surface 7 at one end, e.g. approximately in the lower third of the axial length of the guide piece 3. Each end face of the guide piece 3 is also provided with slits 8, 9, respectively, for engagement with an insertion tool 10.

The expandable anchoring element 14 has a thread 13 within an inner cavity 15 for threadably receiving the thread 6 of the guide piece 3. The anchoring element also has a tapered internal surface at a lower end of the cavity 15, e.g. in the lower third of the element 14. The tapered surface has a taper suitable to permit mating of the tapered surface 7 of the guide piece 3 as described below.

The anchoring element 14 is of hollow cylindrical shape and is provided with a plurality of longitudinal slits 16 at the end which surrounds the guide piece 3. These slits 16 serve to facilitate expansion of the element 14 upon threading of the guide piece 3 into the cavity 15 of the anchoring element 14. The anchoring element 14 also has slits or depressions 17, 18 in the end faces for receiving an insertion tool 11.

The anchoring element 14 may also have a means on the outer circumferential surface for promoting adhesion to a bone. This means may be in the form of a serration 19 or in the form of individual nubby projections. Other surface structures may also be provided to promote adhesion in the cortical bone tissue 2.

The guide piece 3 and anchoring element 14 may be made of any suitable material used in the implantation of prosthesis. For example, these two components of the retention device may be made of polyethylene, for example of the classification HDPE or UHMW.

In order to introduce the retention device into the medullary cavity 1 of the bone 2, the guide piece 3 and anchoring element 14 are first fastened to the two tools 10, 11. In this state, as indicated in FIG. 1, the tools 10, 11 are concentric to each other and to the axis of the retention device. In addition, where the surgically prepared medullary cavity has a large enough opening for the joint introduction of the two components of the retention device, the guide piece 3 and anchoring element 14 are threaded together. The retention device is then inserted into the bone 2 to the intended axial distance from the edge of the opened bone. This axial distance may be established, for example, by a mark on the holding tool 11 for the anchoring element 14. Next, the anchoring element 14 is held via the tool 11 and the guide piece 3 is threaded into the anchoring element 14 via the tool 10, which has a handle 20, far enough that the shell portion provided with the slits 16 is expanded and pressed against the cortical bone tissue 2 with sufficient force to insure fixing of the retention device in place. After release of the tools 10, 11 from the retention device, the shank 4 (see FIG. 3) can be pushed into the cavity 5 of the guide piece 3.

The invention thus provides a retention device for centering the shank of an endoprosthesis in a prepared bone cavity in a relatively simple manner.

Further, the invention provides a retention device which is able to center a shank of an endoprosthesis within a bone having cavities of variable size in a relatively accurate manner.

A guide piece being in threaded engagement with the anchoring element and receiving a shank of non-circular cross-section may be positioned correctly within an anchoring element in a particular plane in virtue of the clearance or lost motion of its thread and/or of the ductility of the materials.

What is claimed is:

1. A retention device for centering an endoprosthesis shank in a bone, said retention device comprising
a guide piece having a cavity extending therethrough for slidably receiving the shank in slide fit relation, and
an expandable anchoring element receiving said guide piece therein in wedge-like relationship.

2. A retention device as set forth in claim 1 wherein said anchoring element has a plurality of longitudinally disposed slits to permit expansion thereof.

3. A retention device as set forth in claim 2 wherein said anchoring element is a deformable hollow cylinder having an undular circumferential surface.

4. A retention device as set forth in claim 1 wherein said anchoring element is a deformable hollow cylinder having an undular circumferential surface.

5. A retention device as set forth in claim 1 wherein said guide piece is threaded into said anchoring element.

6. A retention device for centering a shank of an endoprosthesis in a bone, said device comprising
a guide piece having a central bore extending therethrough defining a cavity for slidably receiving the shank in a slide fit relation; and
an expandable anchoring element having said guide piece secured therein in wedge-like relationship.

7. A retention device as set forth in claim 6 wherein said guide piece is of cylindrical shape with a tapered outer surface at an end received in said anchoring element.

8. A retention device as set forth in claim 7 wherein said anchoring element has a plurality of longitudinal slits at an end circumferentially surrounding said end of said guide piece and a tapered internal surface engaging with said end of said guide piece in wedge-like relation.

9. A retention device as set forth in claim 6 wherein said guide piece and said anchoring element are in threaded engagement.

10. A retention device as set forth in claim 6 wherein said anchoring element has means on an outer circumferential surface for promoting adhesion to a bone.

11. A retention device as set forth in claim 6 wherein said guide piece and said anchoring element each include slits in at least one end face thereof for receiving an insertion tool.

12. A retention device as set forth in claim 6 wherein said guide piece and said anchoring element are made of polyethylene.

13. A retention device as set forth in claim 6 wherein said guide piece is of cylindrical shape with a tapered outer surface at an end received in said anchoring element and said anchoring element has a plurality of longitudinal slits at an end circumferentially surrounding said end of said guide piece and a tapered internal surface engaging with said end of said guide piece in wedge-like relation.

14. A retention device as set forth in claim 13 wherein said guide piece and said anchoring element are in threaded engagement.

15. A retention device as set forth in claim 14 wherein said guide piece and said anchoring element each include slits in at least one end face thereof for receiving an insertion tool.

16. In combination,
a shank of an endoprosthesis; and
a retention device for centering said shank in a bone, said retention device including a guide piece having a cavity extending therethrough for slidably receiving said shank in slide fit relation and an expandable anchoring element receiving said guide piece therein in wedge-like relation.

* * * * *